United States Patent [19]

Holmgreen et al.

[11] Patent Number: 5,024,220
[45] Date of Patent: Jun. 18, 1991

[54] NASOTRACHEAL TUBE INSERTION CONNECTOR

[75] Inventors: W. Corbett Holmgreen; Leonid Bunegin, both of San Antonio, Tex.

[73] Assignee: Board of Regents, The University of Texas System, Austin, Tex.

[21] Appl. No.: 222,550

[22] Filed: Jul. 21, 1988

[51] Int. Cl.⁵ .................. A61M 16/04; A61M 25/02; A61M 39/00
[52] U.S. Cl. .................. 128/207.18; 128/200.26; 128/207.14; 128/911; 128/912
[58] Field of Search ................. 285/258, 382.4, 382.5; 604/905, 283; 128/200.26, 202.27, 204.18, DIG. 26, 911, 912, 207.14, 207.15, 207.16, 207.17, 207.18

[56] References Cited

U.S. PATENT DOCUMENTS

| | | | |
|---|---|---|---|
| 228,161 | 6/1880 | Adlam, Jr. | 285/258 |
| 388,705 | 6/1888 | Grosshandler | 128/207.14 |
| 2,071,478 | 2/1937 | Wick | 285/258 |
| 2,947,409 | 8/1960 | Dodge, Jr. et al. | 285/258 |
| 3,345,730 | 10/1967 | Laverty | 285/382.5 |
| 3,388,705 | 6/1968 | Grosshandler | 604/283 |
| 3,532,365 | 10/1970 | Kronschnabel | 285/258 |
| 3,565,078 | 2/1971 | Vailliancourt | 604/283 |
| 3,606,669 | 9/1971 | Kemble | 128/200.26 |
| 4,076,280 | 2/1978 | Young | 285/39 |
| 4,146,034 | 3/1979 | Gupta | 128/351 |
| 4,297,995 | 11/1981 | Golub | 128/DIG. 26 |
| 4,445,716 | 5/1984 | Hoffman | 285/55 |
| 4,502,482 | 3/1985 | DeLuccia et al. | 128/207.14 |
| 4,593,690 | 6/1986 | Sheridan et al. | 604/283 |
| 4,621,634 | 11/1986 | Nowacki et al. | 128/204.18 |
| 4,850,348 | 7/1989 | Pell et al. | 128/207.15 |

Primary Examiner—Clifford D. Crowder
Assistant Examiner—Kimberly L. Asher
Attorney, Agent, or Firm—Arnold, White & Durkee

[57] ABSTRACT

A flexible tube connector adapted for use in delivering a general anesthesia to patients via a nasotracheal tube is disclosed. More specifically, the present invention relates to a quick insertion nasotracheal tube connector which is designed to facilitate access to the oral cavity and face.

31 Claims, 2 Drawing Sheets

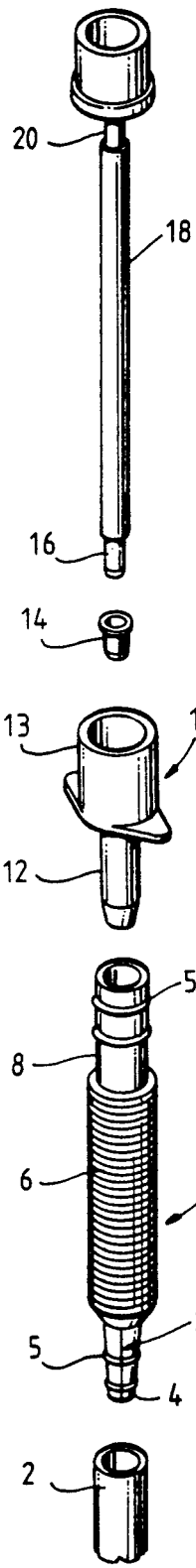
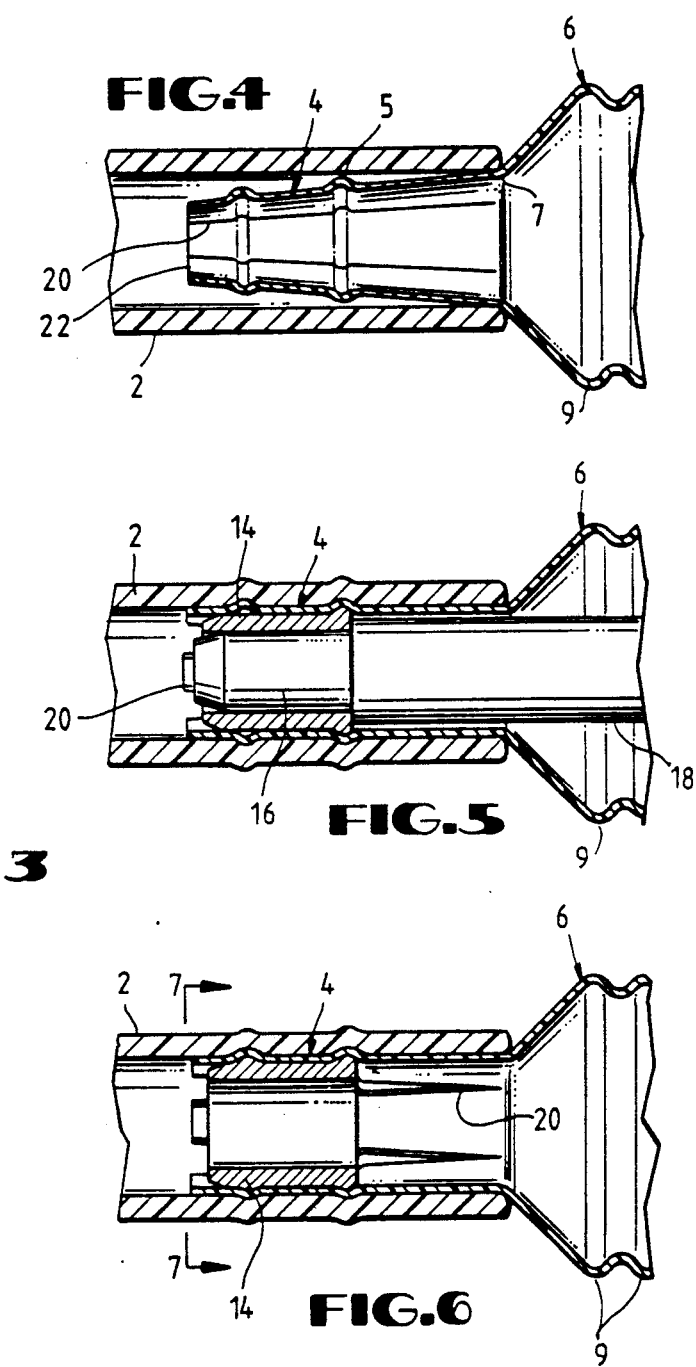
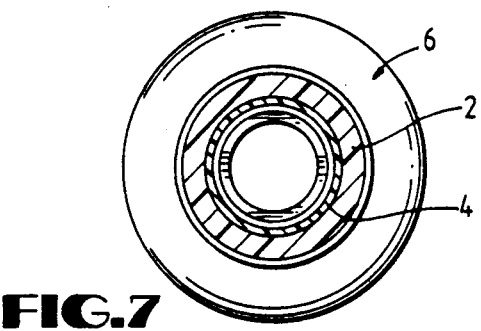

NASOTRACHEAL TUBE INSERTION CONNECTOR

BACKGROUND OF THE INVENTION

1. Field of the Invention

The present invention relates generally to a flexible tube connector adapted for use in delivering a general anesthesia. More specifically, the present invention relates to a quick insertion, nasotracheal tube connector which is designed to facilitate surgical access to the oral cavity and face, while reducing the likelihood of tissue damage to these areas during both intubation and use of the anesthesia system.

2. Description of the Prior Art

Patients who undergo oral or facial surgical procedures often must be anesthetized via a nasotracheal or endotracheal tube. The nasotracheal tube is preferred to the oral endotracheal tube because it allows surgeons and other medical personnel better access to the face or oral cavity. A nasal tube also permits the closure of the mouth during the surgical procedure, thereby facilitating occlusal assessment.

In application, the nasotracheal tube is inserted through the nose, wherein it curves into the oral pharynx, and passes through the vocal cords into the trachea. A cuff or balloon is inflated once the tube is in place, thus protecting the airway from aspirated blood and other secretions which might accumulate during the surgical procedure. Once the nasotracheal tube is thus positioned, it is cut at the level of the nose such as to enable the insertion of an acute, angled connector or "curved connector". This "curved connector" allows the anesthesia supply tubes to be carried close to the patient's face and out of the surgeon's operative field.

Problems, however, commonly arise in inserting the curved connector into the nasotracheal tube. For example, the rigid curved connector is often difficult to insert into the cut end of the plastic nasotracheal tube. In order to insert this connector, considerable force must often be applied against the tube, thus often resulting in tissue damage to both the nose and areas of the upper throat. Further, failure to successfully couple the tube and the connector may result in tissue damage if the connector slips out of the nasotracheal tube and impacts against the facial structures. Additionally, the process of cutting the nasotracheal tube itself may be fraught with potential complications resulting in damage to the nose, eyes and face of the patient.

Various attempts have been made in the art toward the design of a connector that minimizes the aforementioned hazards. One such solution is a preformed (pre-curved) nasotracheal tube. Although such tubes are adequate in many instances, there are many occasions when the predetermined curve in the nasotracheal tube is at an improper distance to the facial region thereby resulting in excessive pressure on the sensitive tissues of the nasal region. In such instances, the nasotracheal tube must be removed and the patient must be reintubated. Reintubation of the tracheal tube, however, is often difficult and may result in needless tracheal trauma. Likewise, the predetermined curve in the tube may be such that the distance between the face and the tube is too great, thereby making the entire assembly very bulky. Such bulk often interferes with proper surgical access to the operative field.

SUMMARY OF THE INVENTION

The present invention addresses the above described and other disadvantages by providing a flexible nasotracheal or endotracheal tube connector which is adapted to easily, yet securely, fit in either type of tracheal tube while reducing the risk of tissue damage to either the nasal region or the surrounding facial structures.

Structurally, the present invention is comprised of a corrugated metal or plastic conduit of a sufficient diameter to permit adequate gas flow with low flow resistance. The conduit is provided with a female end and a male end, the male end having a slotted conical tip of sufficient diameter to easily fit in the intubated nasotracheal or endotracheal tube. The female end is adapted to receive a standard endotracheal tube—anesthesia tubing connector. The conduit is preferably provided with a plurality of fine corrugations disposed about a substantial portion of its length. These corrugations enable the connector to be acutely bent at a desired distance from the face of a patient, thus allowing maximum access to the operative field. The corrugated portion of the conduit resembles a cylindrical bellows which is flexible but also reinforced to retain its cylindrical shape when flexed.

The connector is held in the nasotracheal or endotracheal tube via an expansion or squeeze collar which is adapted to fit within the upper end of the tapered, insertion tip. Placement of the expansion collar within the tip preferably expands or squeezes the conical tip to a diameter greater than that of the nasotracheal tube in which it is inserted, thus resulting in an airtight, strong connection between the tube and the connector.

The present invention has many advantages over the art. One such advantage is the ease with which the present connector may be inserted into the cut end of a nasotracheal or endotracheal tube, thereby avoiding possible damage to the facial tissues.

A second advantage of the present invention is the ability of the connector to be bent or contoured at an optimum distance from the patient's face, thus allowing maximum access to the face and oral cavity by the operating surgeon.

BRIEF DESCRIPTION OF THE DRAWINGS

A preferred and practical embodiment of the present invention is shown in the accompanying drawings, in which:

FIG. 3 is an exploded, perspective view of the component parts of the invention.

FIG. 4 is a side detail view of the connector prior to actuation of the expansion collar.

FIG. 5 is a side detail view of the connector subsequent to insertion of the expansion collar.

FIG. 6 is a side detail view of the connector after the insertion stylet is removed.

FIG. 7 is an end cross-section of the connector as taken through line 7—7 in FIG. 6.

DETAILED DESCRIPTION OF PREFERRED EMBODIMENT

Figure 1:
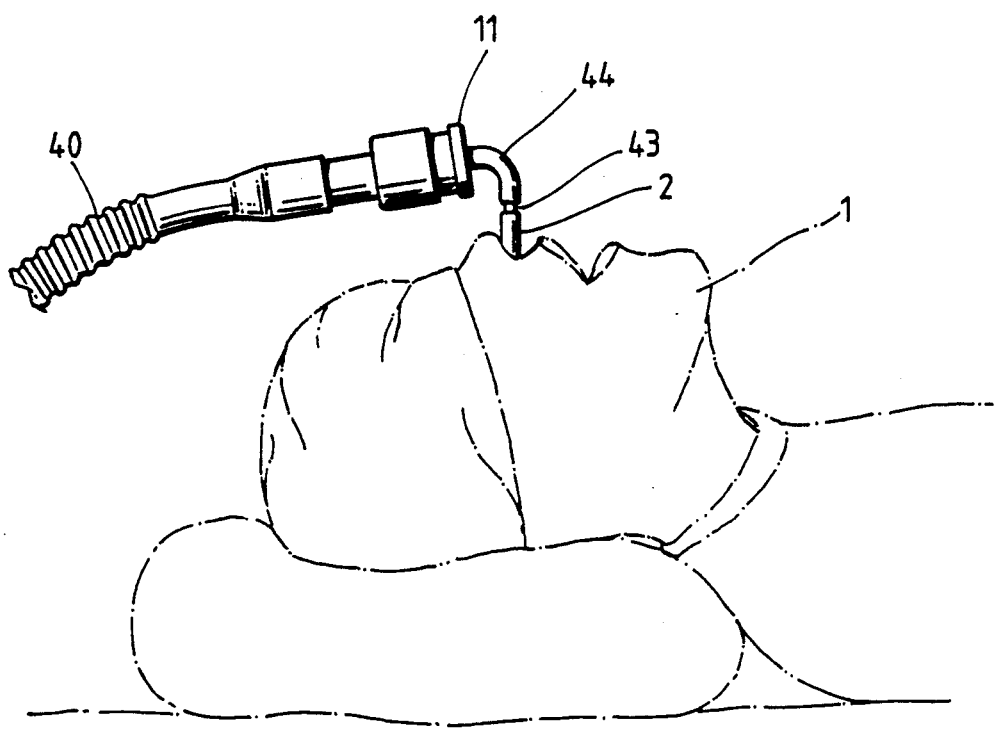
FIG. 1 is a side elevational view of a prior art connector as it may be utilized in association with a nasotracheal tube.

FIG. 1 generally illustrates a prior art connector or "curved connector" 44, such as manufactured by Dupaco or Sheraton, as it is generally utilized in association with contemporary nasotracheal or endotracheal tubes 2. In FIG. 1 the end portion of the nasotracheal tube 2 has been positioned in the nasal passage of the patient 1 and then clipped or cut preparatory to connection to the anesthesia supply system 40 via said curved connector 44. Generally, the connector 44 is coupled to said anesthesia supply systems 40 via anesthesia tubing connector 11.

While the connector 44 in FIG. 1 is preformed or pre-curved to allow the anesthesia supply system 40 to assume a more or less right angle with the nasotracheal tube 2, the inherent weight of system 40 still places an undesired strain on the nasal tissues of the patient. The general end structure of connector 44 also makes its insertion in the nasotracheal tube 2 difficult, often resulting in the risk of both hard and soft tissue damage. Finally, the preformed connector 44 is bulky and is carried at too great a distance from the patient's face, thus hampering the surgeon's operative field.

The component parts of the present invention in relation to conventional anesthesia connectors with which the invention may be used, may be seen by reference to FIG. 3 which illustrates an exploded view of the connector 3 as it may be interfitted between a standard endotracheal tube 2 and an anesthesia tubing connector 11. Structurally, connector 3 comprises a hollow tube or conduit having a tapered insertion tip or male end 4 and a receiving or female end 8. The male or patient end 4 is 1 preferably sufficiently expandable to be squeezed or forced radially outward.

Referring to FIGS. 3-6, tapered tip 4 is preferably provided with longitudinal slits or grooves 20. Such slits 20 are preferably placed symmetrically around the tip 4 so as to define independently moveable segments 22. As thus formed, tip segments 22 are able to independently expand in a radial direction upon insertion of the expansion collar 14 as will be further described herein.

In preferred embodiments, both the patient end or tip 4 and the remote or receiving end 8 of the connector 3 are provided with corrugations 5 to enhance the flexibility and hence adaptability of the connector 3. Such corrugations or buttresses 5 also help the connector 3 maintain its circular shape. Further, such corrugations help secure tip 4 in tube 2 upon actuation of expansion collar 14. The internal ends of the segments 22 preferably do not extend as far as the external end of the tube 2.

Figure 2:
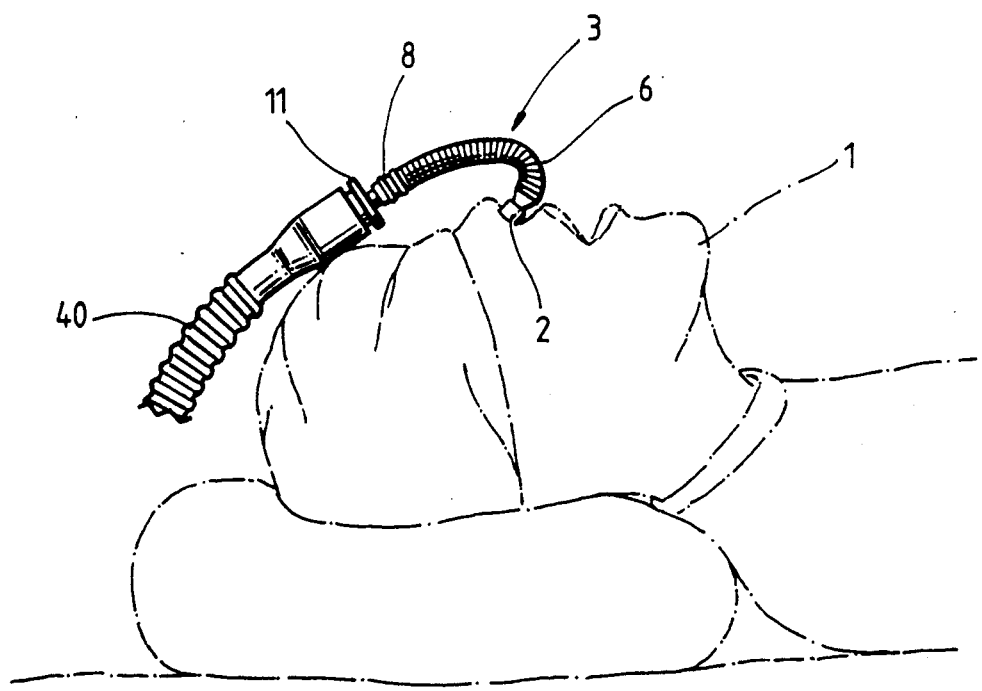
FIG. 2 is a side elevational view of the present invention as it may be utilized in association with a nasotracheal tube.

In a general embodiment, a corrugated or bellows-like segment 6 is disposed between the tapered tip 4 and the female end 8 of the connector 3. The length of this segment 6 may be variable dependent on its desired application. Preferably, however, this corrugated or bellows segment 6 should be of sufficient length so as to allow for an acute bend in the segment without resulting in a constriction of the air flow therethrough. Alternately, this corrugated segment 6 should be of a sufficient length so that upon being bent or flexed to a desired operating configuration relative to the patient 1, connector 3 (and thus tube 2) will not exert undue pressure on the nasal tissues. (See FIG. 2.)

As illustrated in FIG. 3, the corrugated segment 6 may possess a larger outer diameter than the outer diameter of the semi-rigid female end 8. It is envisioned, however, that an alternate embodiment may be desired where the corrugated segment 6 is provided with an outer diameter less than or equal to the maximum outside diameter of the female segment 8. Variations in the diameter of such corrugations may be desired depending upon whether an endotracheal or nasotracheal application is envisioned. In all cases, however, relatively fine corrugations 9 of this segment 6 are desired, e.g., at least one corrugation per millimeter along the segment 6.

The remote end 8 of connector 3 may be attached to an anesthesia supply 40 via a conventional anesthesia tubing connector 11. As illustrated, such connectors generally include a female end 13 and a male end 12. The male end 12 is adapted to fit in the female end 8 of connector 3. The female end 13 of the anesthesia tubing connector 11 is then coupled to an anesthesia supply 40 via conventional coupling. (See FIG. 2)

As earlier described, the tapered tip 4 of connector 3 is adapted to receive an expansion collar 14. Once the tip 4 is inserted in tube 2, placement of the expansion collar 14 within tip 4 results in a substantially airtight fit between the connector 3 and the tube 2. The expansion collar 14 effectively squeezes and seats the tip 4 against the tube 2.

As may be seen by reference to FIG. 3, the collar 14 itself is preferably hollow and fluted in shape with its smaller diameter at the patient or insertion end of collar 14. In a preferred embodiment, expansion collar 14 is carried by a plunger or stylet 18. Preferably, stylet 18 is hollow so as to allow for ventilation through its length should there develop a need to ventilate the patient during placement of the collar 14. To enhance the mounting and placement of collar 14, stylet 18 may be provided with a recessed portion 16 at its terminal end.

In a general embodiment, expansion collar 14 is inserted in the nasotracheal tube 2. Mounted on the stylet 18, expansion collar 14 is inserted through the open female end 8 of the connector into tapered tip 4 resulting in an expansion of tip 4. Upon insertion of collar 14, individual segments 22 are expanded radially outward into binding engagement with the inner wall of tube 2. Insertion of collar 14 causes a uniform expansion of tube 2, resulting in a substantially airtight fit or seal between connector 3 and tube 2. The fluted shape of expansion collar 14 fixes the position of the connector in tube 2 once stylet 18 is extracted. Such affixation is also enhanced by the presence of buttresses 5.

The process by which the connector 3 may be manually inserted and secured in a nasotracheal tube 2 may be seen by reference to FIGS. 4-7. As a preliminary procedure, the nasotracheal tube 2 is intubated in the patient 1 and then clipped so that a minimum length of the tube 2 protrudes from the nose. The tapered insertion tip 4 of the connector 3 is then inserted in the tube 2 until the inner diametrical extent of tube 2 contacts shoulder 7 as shown in FIG. 4. Expansion collar 14 is then mounted on stylet 18 and inserted through the female end 8 of the connector. The stylet 18 is then pushed until fully seated in tip 4. Preferably, seating occurs when the larger, trailing end of the collar 14 engages the inner surface of a buttress 5. The insertion of collar 14 expands slotted tip 4 and tube 2, resulting in an airtight fit therebetween. Stylet 18 is then withdrawn and a conventional anesthesia tubing connector (not shown) is then connected to the female end 8 of the connector.

In a preferred embodiment, connectors may be comprised of a self-contained, integrated unit or kit including both the stylet, collar and connector, where such elements are pre-assembled, sterilized and prepackaged to enhance efficiency of application. In such a unit or kit, the collar 14 is detachably mounted on the stylet. Following seating of the collar 14 in a tracheal tube, the stylet is detached from the collar and withdrawn from the connector and the remote end of the connector then connected to a source of anesthesia, oxygen, or other gas.

It is envisioned that such units may be made out of a radiographically transparent or translucent plastic which may be sterilized and prepackaged prior to use.

What is claimed is:

1. A connector for coupling a tracheal tube to a supply of anesthesia gas, comprising:
    a tubular body including along its length a flexible, peripherally integrious portion, said body defining a remote end having means for connecting said body to a supply of anesthesia gas, and a patient end terminating in an expandable, tapered tip to facilitate insertion of said body in a tracheal tube; and
    an expansion collar adapted to be inserted and secured totally within said tip and configured to increase the diameter of said tip when inserted in the tracheal tube, such that the insertion of said collar in said tip results in a secure, substantially airtight fit between said connector and said tube, said collar, when inserted totally within said tip, defining a first and second free end not used as a connecting means.

2. The connector of claim 1 wherein said tapered tip includes longitudinal slots or grooves peripherally spaced to define radially expandable segments.

3. The connector assembly of claim 1 further comprising a handle detachably attached to said collar.

4. The connector of claim 1 wherein the body and the collar are comprised of a radiographically transparent or translucent material.

5. The connector of claim 1 wherein the cross section of said collar is such that longitudinal movement of said collar into said tip results in an expansion of said tip to an outer diameter greater than the inner diameter of the tracheal tube.

6. The connector of claim 1 wherein said flexible, peripherally integrious portion comprises a plurality of corrugations radially disposed along said portion.

7. The connector of claim 1 wherein said flexible, peripherally integrious portion of the body has an outer diameter at least equal to the outer diameter of the patient end.

8. The connector of claim 1 wherein the expansion collar is fluted in shape, and has a larger diameter portion and a smaller diameter portion.

9. The connector of claim 8 wherein the smaller diameter portion of the collar is held in the patent end of said tip.

10. The connector of claim 1 wherein the flexible, peripherally integrious portion includes at least one radially disposed corrugation per millimeter.

11. The connector of claim 1 wherein the peripherally integrious portion of said body is sufficiently flexible to enable the body to assume an acute angle relative to itself without flow restriction therethrough.

12. A connector for coupling a nasotracheal tube to an anesthesia source, comprising:
    a tubular body having a patient end defining an expandable tapered tip, and a remote end adapted to be coupled to an anesthesia source;
    an expansion collar adapted to slidably fit within said tip and to increase the outer diameter of said tip sufficiently to form a substantially airtight fit between said connector and said tracheal tube; and
    means attachable to the collar to position said collar in said body.

13. The connector of claim 12 wherein the position means comprises a hollow plunger.

14. The connector of claim 12 wherein the tapered tip includes longitudinal slots or grooves formed along its length and spaced so as to define independent segments capable of undergoing radial expansion.

15. The connector of claim 12 further including a flexible, corrugated portion capable of enabling the body to be bent without radial constriction of said portion.

16. The connector of claim 12 further comprising a series of corrugations radially disposed along the body.

17. The connector of claim 12 wherein both the body and the collar are comprised of radiographically transparent or translucent materials.

18. The connector of claim 12 wherein longitudinal movement of said collar into said tip results in an expansion of said tip to an outer diameter greater than the inner diameter of said nasotracheal tube.

19. The connector of claim 12 wherein the expansion collar is fluted in shape, said collar having a larger and a smaller diameter portion, said smaller diameter portion held in the patient end of said tip.

20. The connector of claim 19 wherein said collar is hollow so as to allow for air flow therethrough.

21. A connector for coupling a nasotracheal tube to a supply of anesthesia gas, comprising:
    a tubular body including along its length a flexible, corrugated portion, said body defining a remote end having means for connecting said tube to a supply of anesthesia gas, and a patient end tapered and longitudinally slotted to facilitate the insertion of said body in said tube; and
    an expansion collar adapted to be inserted and seated totally within said tip, said collar defining a longitudinal bore so as to enable gas flow therethrough when said collar is secured totally within said tip, said collar, when seated totally within said tip, defining a first and second free end not used as a connecting means.

22. The connector of claim 21 further including means to position said collar in said tip.

23. The connector of claim 22 wherein said means comprises a hollow stylet.

24. The connector of claim 21 wherein in said slots are spaced to define individual, radially expandable segments.

25. The connector of claim 21 wherein the longitudinal movement of said collar in said tip results in an expansion of said tip to an outer diameter greater than the inner diameter of the nasotracheal tube.

26. The connector of claim 21 wherein the body and the collar are comprised of a radiographically transparent or translucent material.

27. A connector for connecting a tracheal tube to a gas supply, comprising:
    a conduit having a first end adapted to be connected to a gas supply; a central section which is bendable, but peripherally integrious; and a second end which is radially enlargeable but reduced in internal diameter relative to said first and the central portion and also adapted to enter within a tracheal tube;

a collar member adapted to enter the second end of the conduit, to move through the central section, and to squeeze the second end radially outward to seat against an inner wall surface of the tracheal tube and resist relative axial movement between the tracheal tube, the second end, and the collar member, said collar member when inserted totally within said second end of said conduit defining a first and second free end not used as a connecting means.

28. The connector of claim 27 wherein an outer surface of the collar member and an inner surface of the second section are configured to inter-engage one another when in a seated relation so as to resist relative axial movement.

29. The conduit of claim 27 wherein the central section is bellows-shaped.

30. The conduit of claim 27 further comprising a stylet attachable to the collar member and adapted to move the collar member within the conduit.

31. The conduit of claim 27 wherein the second end has a plurality of spaced, longitudinally disposed slots extending from the tip of the second end to divide the second end into longitudinally disposed segments.

* * * * *

UNITED STATES PATENT AND TRADEMARK OFFICE
CERTIFICATE OF CORRECTION

PATENT NO.   :   5,024,220
DATED        :   June 18, 1991
INVENTOR(S)  :   Holmgreen et al.

It is certified that error appears in the above-identified patent and that said Letters Patent is hereby corrected as shown below:

In claim 24, at column 6, line 55, delete the word "in".

In claim 27, at column 7, line 3, insert --end-- between "first" and "and".

Signed and Sealed this

Third Day of November, 1992

Attest:

DOUGLAS B. COMER

*Attesting Officer*    *Acting Commissioner of Patents and Trademarks*